US00PP17964P2

(12) United States Plant Patent
Dekker

(10) Patent No.: US PP17,964 P2
(45) Date of Patent: Aug. 28, 2007

(54) ***CHRYSANTHEMUM* PLANT NAMED 'MONA LISA ROSY'**

(50) Latin Name: *Chrysanthemum×morifolium*
Varietal Denomination: Mona Lisa Rosy

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 82 days.

(21) Appl. No.: 11/259,312

(22) Filed: Oct. 26, 2005

(51) Int. Cl.
*A01H 5/00* (2006.01)

(52) U.S. Cl. ..... Plt./291

(58) Field of Classification Search ..... Plt./291
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Mona Lisa Rosy', characterized by its double anemone-type inflorescences with elliptic-shaped, pink-colored ray florets; strong and upright flowering stems; freely flowering habit; early and uniform flowering response; and good postproduction longevity.

1 Drawing Sheet

Botanical designation: *Chrysanthemum×morifolium.*
Cultivar denomination: 'Mona Lisa Rosy'.

BACKGROUND OF THE INVENTION

The present invention relates to a new and distinct cultivar of *Chrysanthemum* plant, botanically known as *Chrysanthemum×morifolium* and referred to by the name 'Mona Lisa Rosy'.

The new *Chrysanthemum* is a naturally-occurring whole plant mutation of the *Chrysanthemum×morifolium* cultivar Mona Lisa Pink, not patented. The new *Chrysanthemum* was discovered and selected by the Inventor in April, 2003 as a single flowering plant within a population of plants of the parent selection in a controlled environment in Hensbroek, The Netherlands.

Asexual reproduction of the new *Chrysanthemum* by terminal cuttings in Hensbroek, The Netherlands since May, 2003, has shown that the unique features of this new *Chrysanthemum* are stable and reproduced true to type in successive generations.

BRIEF SUMMARY OF THE INVENTION

The cultivar Mona Lisa Rosy has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Mona Lisa Rosy'. These characteristics in combination distinguish 'Mona Lisa Rosy' as a new and distinct cultivar:

1. Double anemone-type inflorescences with elliptic-shaped, pink-colored ray florets; typically grown as a spray-type.
2. Strong and upright flowering stems.
3. Freely flowering habit.
4. Early and uniform flowering response.
5. Good postproduction longevity.

Plants of the new *Chrysanthemum* can be compared to plants of the parent, the cultivar Mona Lisa Pink. In side-by-side comparisons conducted in Hensbroek, The Netherlands, plants of the new *Chrysanthemum* differed from plants of the cultivar Mona Lisa Pink primarily in ray floret coloration as plants of the new *Chrysanthemum* have darker pink-colored ray florets.

Plants of the new *Chrysanthemum* can also be compared to plants of the *Chrysanthemum* cultivar Mona Lisa Salmon, disclosed in U.S. Plant patent application Ser. No. 11/118,921. In side-by-side comparisons conducted in Hensbroek, The Netherlands, plants of the new *Chrysanthemum* differed primarily from plants of the cultivar Mona Lisa Salmon in the following characteristics:

1. Leaves of plants of the new *Chrysanthemum* had apiculate apices whereas leaves of plants of the cultivar Mona Lisa Salmon had cuspidate apices.
2. Ray florets of plants of the new *Chrysanthemum* were elliptic in shape whereas ray florets of plants of the cultivar Mona Lisa Salmon were lanceolate in shape.
3. Ray florets of plants of the new *Chrysanthemum* were pink in color whereas ray florets of plants of the cultivar Mona Lisa Salmon were salmon pink in color.
4. Inflorescences of plants of the new *Chrysanthemum* had more ray florets than inflorescences of plants of the cultivar Mona Lisa Salmon.
5. Plants of the new *Chrysanthemum* flowered earlier than plants of the cultivar Mona Lisa Salmon.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Mona Lisa Rosy'.

The photograph at the bottom of the sheet comprises a close-up view of upper and lower surfaces of typical inflorescences and typical leaves of 'Mona Lisa Rosy'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the late summer in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5° C. to 30° C., night temperatures ranged from 18.5° C. to 24° C. and light levels were about five kilolux. Plants were pinched once and were about nine weeks from planting when the photographs and the description were taken.

Botanical classification: *Chrysanthemum×morifolium* cultivar Mona Lisa Rosy.

Commercial classification: Double anemone-type *Chrysanthemum* typically grown as a spray-type cut flower.

Parentage: Naturally-occurring whole plant mutation of the *Chrysanthemum×morifolium* Mona Lisa Pink, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous double anemone-type cut *Chrysanthemum;* typically grown as a spray-type; erect and strong flowering stems. Moderately vigorous growth habit.

*Flowering stem description.*—Length: About 75 cm. Diameter: About 6 mm. Strength: Strong. Texture: Pubescent. Aspect: Erect. Branching habit: Plants are typically grown as single stems. Color: 146A.

*Foliage description.*—Arrangement: Alternate; simple. Length: About 6 cm to 13 cm. Width: About 4 cm to 8.5 cm. Apex: Apiculate. Base: Attenuate. Margin: Palmately lobed. Texture, upper and lower surface: Slightly pubescent. Petiole length: About 5 mm to 30 mm. Color: Developing foliage, upper surface: Close to 139A. Developing foliage, lower surface: Close to 137C. Fully expanded foliage, upper surface: Close to 137A; venation, 137B. Fully expanded foliage, lower surface: Between 137B and 137C; venation, 138B. Petiole, upper and lower surfaces: 138B.

Inflorescence description:

*Appearance.*—Double anemone-type inflorescence form with elliptic-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about seven weeks later. Early and uniform flowering response.

*Postproduction longevity.*—Cut inflorescences will maintain good substance and form for about three weeks.

*Quantity of inflorescences per flowering stem.*—About 25 to 30 inflorescences per flowering stem.

*Inflorescence size.*—Diameter: About 6 cm to 7 cm. Depth (height): About 2 cm. Diameter of disc: About 1 cm to 3 cm.

*Inflorescence buds.*—Height: About 6 mm. Diameter: About 1 cm. Shape: Oblate. Color: 137C.

*Ray florets.*—Length: About 1.5 cm to 3.5 cm. Width: About 7 mm to 13 mm. Shape: Elliptic. Apex: Broadly acuminate. Base: Attenuate. Margin: Entire. Texture, upper and lower surfaces: Smooth, glabrous. Number of ray florets per inflorescence: About 60 in numerous whorls. Color: When opening, upper surface: 69D. When opening, lower surface: N155B. Fully opened, upper surface: Between 69B and 69C. Fully opened, lower surface: 69D.

*Disc florets.*—Shape: Tubular; elongated. Length: About 6 mm to 17 mm. Width: About 6 mm. Number of disc florets per inflorescence: About 75. Color: Immature: 145C. Mature: Apex: 150B. Mid-section: 155D. Base: 145C.

*Peduncles.*—Length, terminal peduncle: About 2.5 cm. Length, fourth peduncle: About 6 cm. Diameter: About 2 mm to 4 mm. Angle: About 45° from vertical. Strength: Strong. Texture: Pubescent. Color: 146A.

*Reproductive organs.*—Androecium: Present on disc florets only. Anther color: Close to 151B. Pollen: None observed. Gynoecium: Present on both ray and disc florets. Stigma length: About 1 mm. Stigma diameter: Less than 1 mm. Stigma color: Close to 151B.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Mona Lisa Rosy', as illustrated and described.

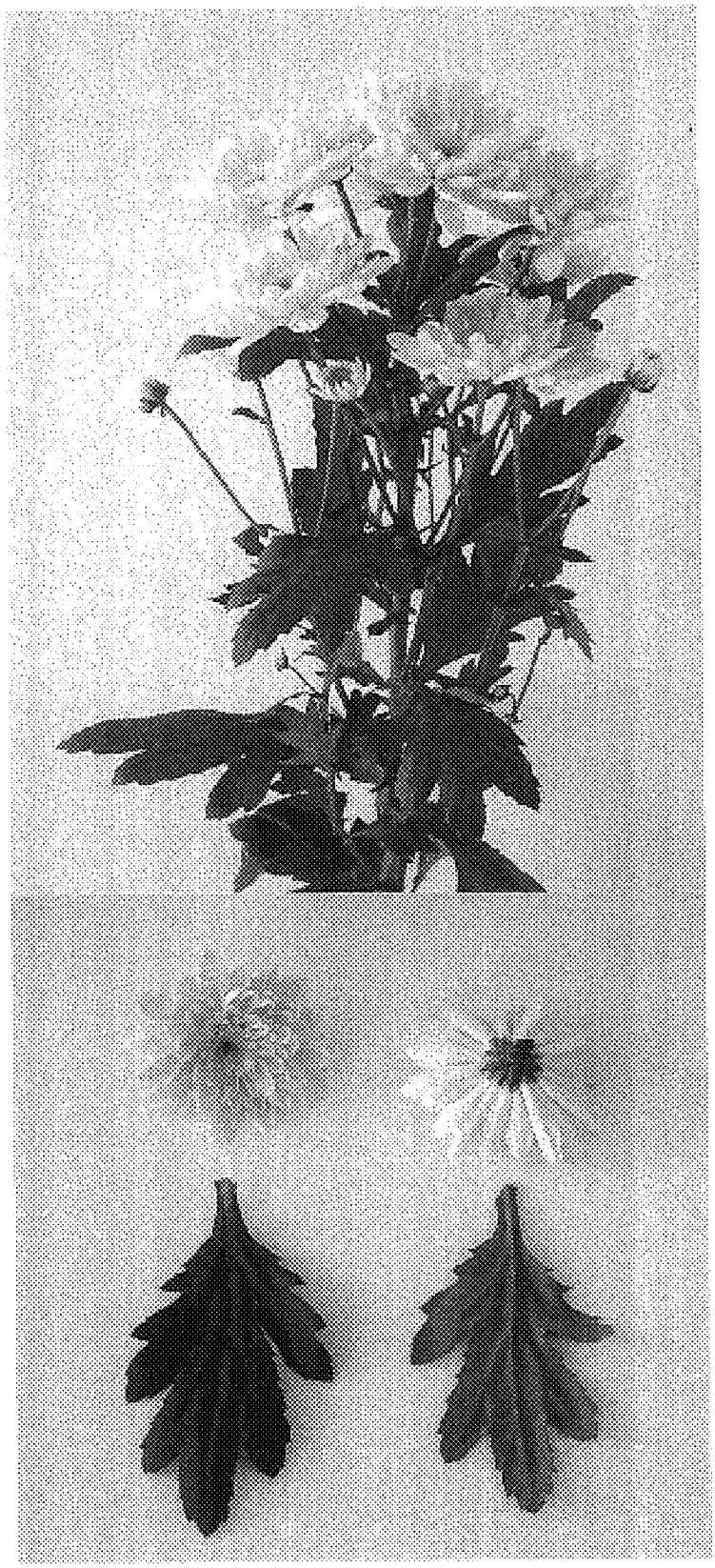

* * * * *